(12) United States Patent
Sasaki et al.

(10) Patent No.: US 8,034,040 B2
(45) Date of Patent: Oct. 11, 2011

(54) PULL-ON DISPOSABLE DIAPER

(75) Inventors: Toru Sasaki, Kagawa-ken (JP); Kyoko Ito, Kagawa-ken (JP)

(73) Assignee: Uni-Charm Co., Ltd., Ehime (JP)

( * ) Notice: Subject to any disclaimer, the term of this patent is extended or adjusted under 35 U.S.C. 154(b) by 1202 days.

(21) Appl. No.: 11/044,291

(22) Filed: Jan. 28, 2005

(65) Prior Publication Data

US 2005/0131378 A1 Jun. 16, 2005

Related U.S. Application Data

(63) Continuation of application No. PCT/JP03/11090, filed on Aug. 29, 2003.

(30) Foreign Application Priority Data

Aug. 30, 2002 (JP) ................. 2002-255986
Aug. 22, 2003 (JP) ................. 2003-208458

(51) Int. Cl.
*A61F 13/15* (2006.01)
*A61F 13/20* (2006.01)
(52) U.S. Cl. ......................... 604/389; 24/304
(58) Field of Classification Search ............. 604/385.01, 604/385.27
See application file for complete search history.

(56) References Cited

FOREIGN PATENT DOCUMENTS

| DE | 3202514 A1 | 9/1982 |
|---|---|---|
| EP | 0925770 A2 | 6/1999 |
| EP | 1454605 A1 | 9/2004 |
| EP | 1541105 A1 | 6/2005 |
| JP | 6-77719 | 11/1994 |
| JP | 10-085254 | 4/1998 |
| JP | 10-085254 A | 4/1998 |
| WO | 95/34266 A1 | 4/1995 |
| WO | 95/34266 | 12/1995 |
| WO | WO 95/34266 * | 12/1995 |
| WO | WO 9534266 A1 * | 12/1995 |

OTHER PUBLICATIONS

EP Search Report issued Sep. 3, 2009.

* cited by examiner

*Primary Examiner* — Melanie Hand
(74) *Attorney, Agent, or Firm* — Lowe, Hauptman, Ham & Berner, LLP

(57) ABSTRACT

A pull-on disposable diaper includes in a waist covering region thereof a tape tab extending in a waist-circumferential direction. The tape tab includes a fixed tape section secured to an outer sheet of the diaper and a movable tape section contiguous to the fixed tape section. The movable tape section has a distal end portion and a proximal end portion. The distal end portion is formed with a finger grip zone and an attaching element located short of this finger grip zone. The proximal end portion is contiguous to one end portion of the fixed tape section. The attaching element is releasably attached to a zone of the fixed tape section in which the fixed tape section is curved to bulge in a direction spaced apart outwardly from an outer surface of the waist covering region.

17 Claims, 9 Drawing Sheets

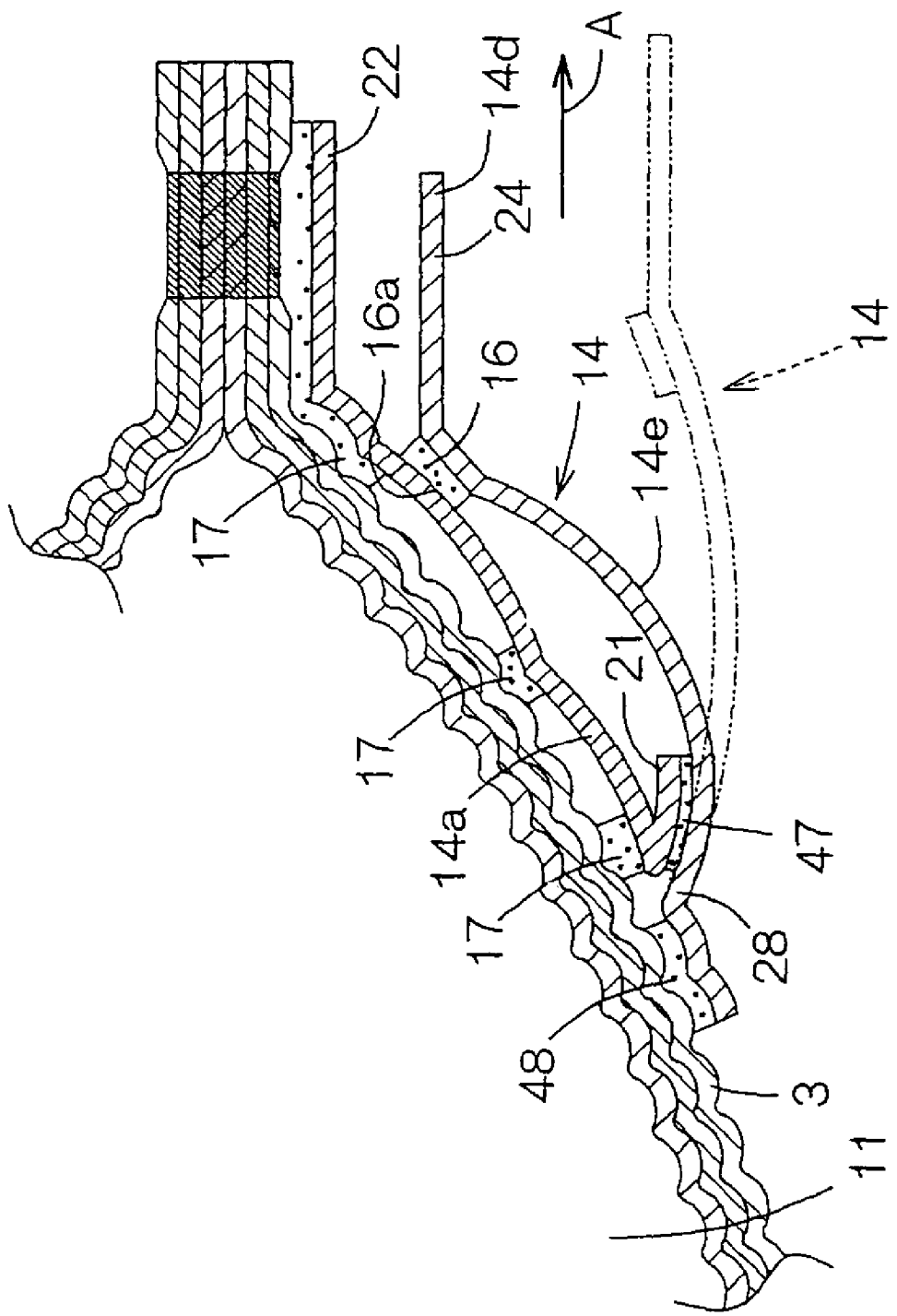

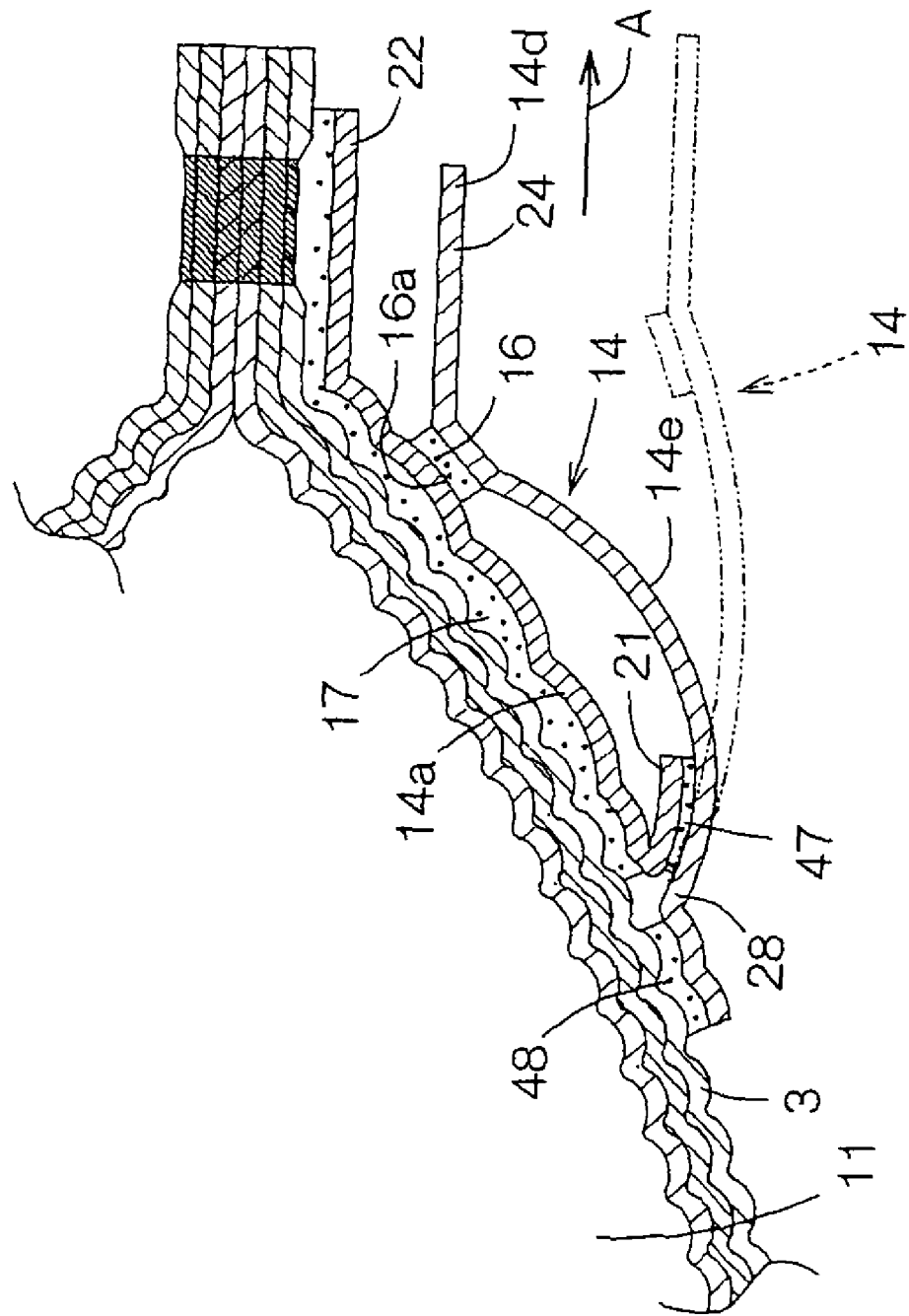

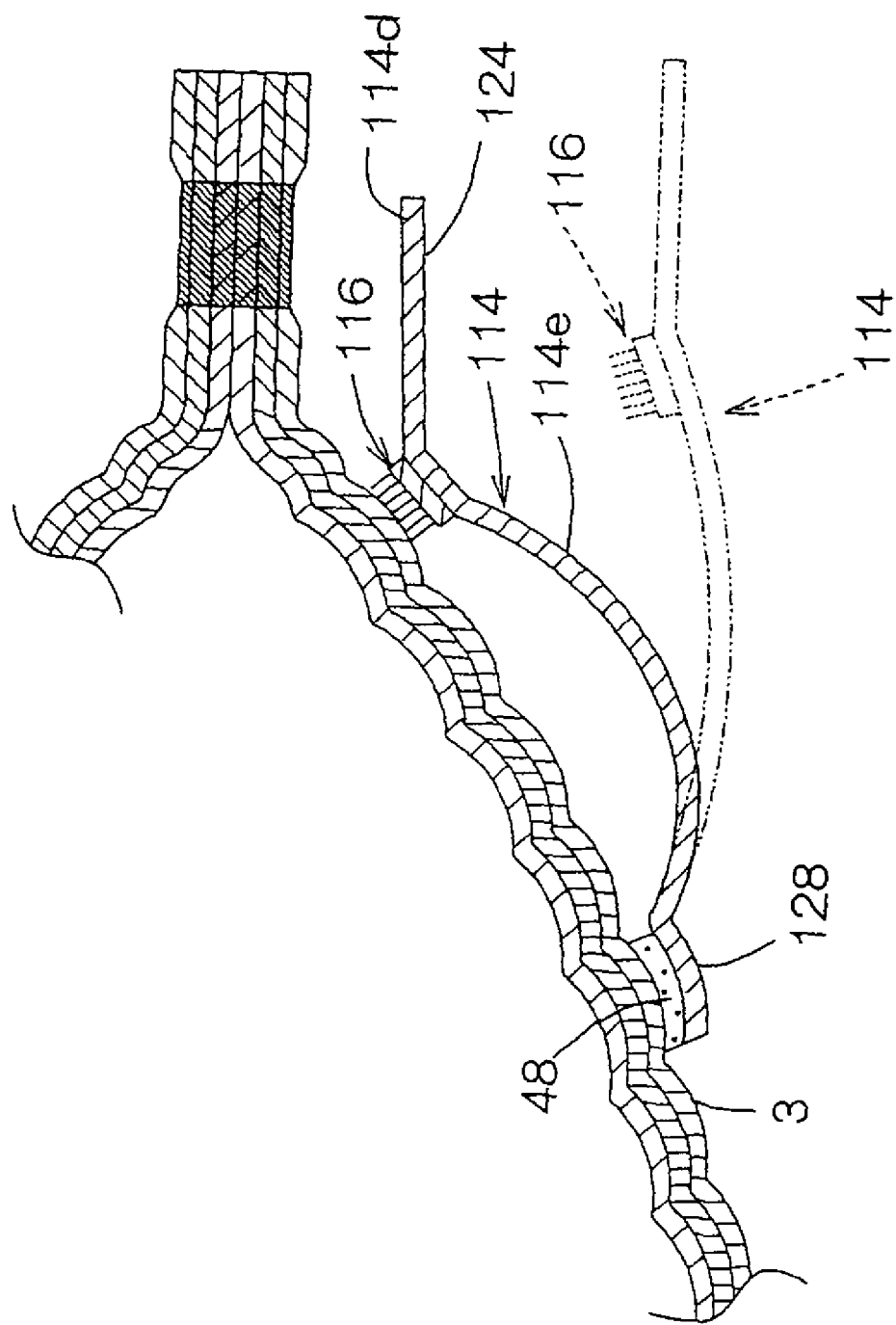

PULL-ON DISPOSABLE DIAPER

BACKGROUND OF THE INVENTION

The present invention relates to a pull-on disposable diaper.

Japanese Utility Model Application Publication No. 1994-77719 A (Reference No. 1).

This Publication discloses a disposable diaper provided with tape fasteners used to retain a used diaper in a rolled up or folded state for disposal thereof. Use of such tape fasteners to retain the used diaper in rolling up or folding state for disposal is sanitarily as well as seemingly preferable since any contaminated regions of the diaper are prevented from being exposed.

The tape fastener in the disposable diaper disclosed by the above-cited Publication is folded in its longitudinal direction in a Z-shape or a reversed Z-shape. To unfold this tape fastener in the longitudinal direction, a troublesome handling is required. Specifically, the tape fastener must be pulled with a finger grip zone held by fingers, first in a direction opposite to a direction in which the finger grip zone points and then in the direction in which the finger grip zone points in order to peel off layers of the folded tape fastener from one another. In this manner, this well-known tape fastener can not be utilized merely by pulling it with the finger grip held between fingers in one and same direction. Correspondingly, the user of the diaper may experience more or less inconvenience for use.

Reference No. 1: Japanese Utility Model Application Publication No. 1994-77719 A

SUMMARY OF THE INVENTION

It is an object of the present invention to provide an improved pull-on disposable diaper having a tape tab whose attaching means applicable to a waist covering region or a crotch covering region is releasably attached to the diaper. According to the present invention, the attaching means is made easy to release.

In the aspect of the present invention, there is provided a pull-on disposable diaper having a waist covering region, a crotch covering region, a waist-hole and a pair of leg-holes and being provided on an outer surface of the waist covering region with a tape tab extending in a waist-circumferential direction of the waist covering region and having an attaching means to be applicable to one of the waist covering region and the crotch covering region.

The present invention further comprises the waist covering region having a part stretchable and contractible in an elastic manner in the waist-circumferential direction and provided with gathers brought by contraction of an elastic member included in the waist covering region and repeating a dent and a bulge one after another in the waist-circumferential direction; and the tape tab comprising a fixed tape section permanently attached to the outer surface and a movable tape section contiguous to the fixed tape section; the movable tape section having a proximal end portion and a distal end portion, the proximal end portion being contiguous to one end of the fixed tape section in the waist-circumferential direction, the distal end portion having a finger grip zone and lying aside to another end portion opposed to the one end portion of the fixed tape section or lying aside to the one end portion in consequence of folding back of the movable tape section in a vicinity of another end portion; the attaching means being formed on an inside surface opposed to the outer surface of the waist covering region and located short of the finger grip zone of the movable tape section; at least a part of the fixed tape section and the movable tape section being curved so as to bulge in a direction spaced apart outwardly from the outer surface of the waist covering region as the waist covering region elastically contracts in the waist-circumferential direction; and the attaching means being releasably attached to the part of one of the fixed tape section and the movable tape section.

The present invention includes the following embodiments.

The one end portion of the fixed tape section is an inner end portion of the tape tab lying aside toward a center line bisecting a width of the diaper, and the end portion opposite to the one end portion is an outer end portion of the tape tab, the movable tape section is folded in two along a fold formed between the distal end portion and the proximal end portion, the movable tape section comprises a first movable tape subsection having the finger grip zone and the attaching means and a second movable tape subsection including the proximal end portion and interposed between the first movable tape subsection and the fixed tape section, the first movable tape subsection is releasably attached to a zone of the second movable tape subsection lying aside to the proximal end portion in the attaching means, and the second movable tape subsection is releasably attached, in a vicinity of the fold, to a zone of the fixed tape section lying aside to the inner end portion and curves so as to bulge in the direction spaced apart outwardly from the outer surface of the waist covering region in a zone to which the attaching means of the first movable tape subsection is releasably attached.

The tape tab comprising the first movable tape subsection, the second movable tape subsection and the fixed tape section is folded in a Z-shape or a reversed Z-shape as viewed in the waist-circumferential direction.

The second movable tape subsection curves so as to bulge in the direction spaced apart outwardly from the outer surface of the waist covering region in a zone between the inner and outer end portions of the fixed tape section in the waist-circumferential direction.

The one end portion of the fixed tape section is an inner end portion of the tape tab lying aside toward a center line bisecting a width of the diaper, and the end portion opposed to the one end portion is an outer end portion of the tape tab, the proximal end portion of the movable tape section lies aside toward the center line and is contiguous to the inner end portion of the fixed tape section, the distal end portion of the movable tape section extends from the inner end portion toward the outer end portion of the fixed tape section and is releasably attached to a zone lying in a vicinity of the outer end portion of the fixed tape section, and the fixed tape section curves in the waist-circumferential direction so that at least the zone of the fixed tape section to which the distal end portion of the fixed tape section is releasably attached bulges in the direction spaced apart outwardly from the outer surface of the waist covering region.

The attaching means is any one of an adhesive and a hook member of a mechanical fastener comprising hook and loop members.

In another aspect of the present invention, there is further provided a pull-on disposable diaper having a waist covering region, a crotch covering region, a waist-hole and a pair of leg-holes and being provided on an outer surface of the waist covering region with a tape tab extending in a waist-circumferential direction of the waist covering region and having an attaching means to be applicable to one of the waist covering region and the crotch covering region.

The present invention further comprises the waist covering region having a part stretchable and contractible in an elastic manner in the waist-circumferential direction and provided with gathers brought by contraction of an elastic member included in the waist covering section and repeating a dent and a bulge one after another in the waist-circumferential direction; the tape tab comprising a fixed tape section permanently attached to the outer surface and a movable tape section contiguous to the fixed tape section, the movable tape section having a proximal end portion and a distal end portion, the proximal end portion being contiguous to one end of the fixed tape section in the waist-circumferential direction, the distal end portion having a finger grip zone and attaching means; the attaching means being formed on the inside surface opposed to the outer surface of the waist covering region and located short of the finger grip zone of the movable tape section; and the attaching means being releasably attached to the bulge of the gathers.

In this aspect of the present invention the attaching means is one of an adhesive and a hook member of a mechanical fastener comprising hook and loop members.

BRIEF DESCRIPTION OF THE DRAWINGS

FIG. 7 is a view similar to FIG. 2, showing further another embodiment of the invention;
FIG. 8 is a view similar to FIG. 7, showing further another embodiment of the invention;
and
FIG. 9 is a view similar to FIG. 8 showing further another embodiment of the invention.

DETAILED DESCRIPTION OF THE PREFERRED EMBODIMENTS

Details of the pull-on disposable diaper according to the present invention will be more fully understood from the description given hereunder with reference to the accompanying drawings.

Figure 1:
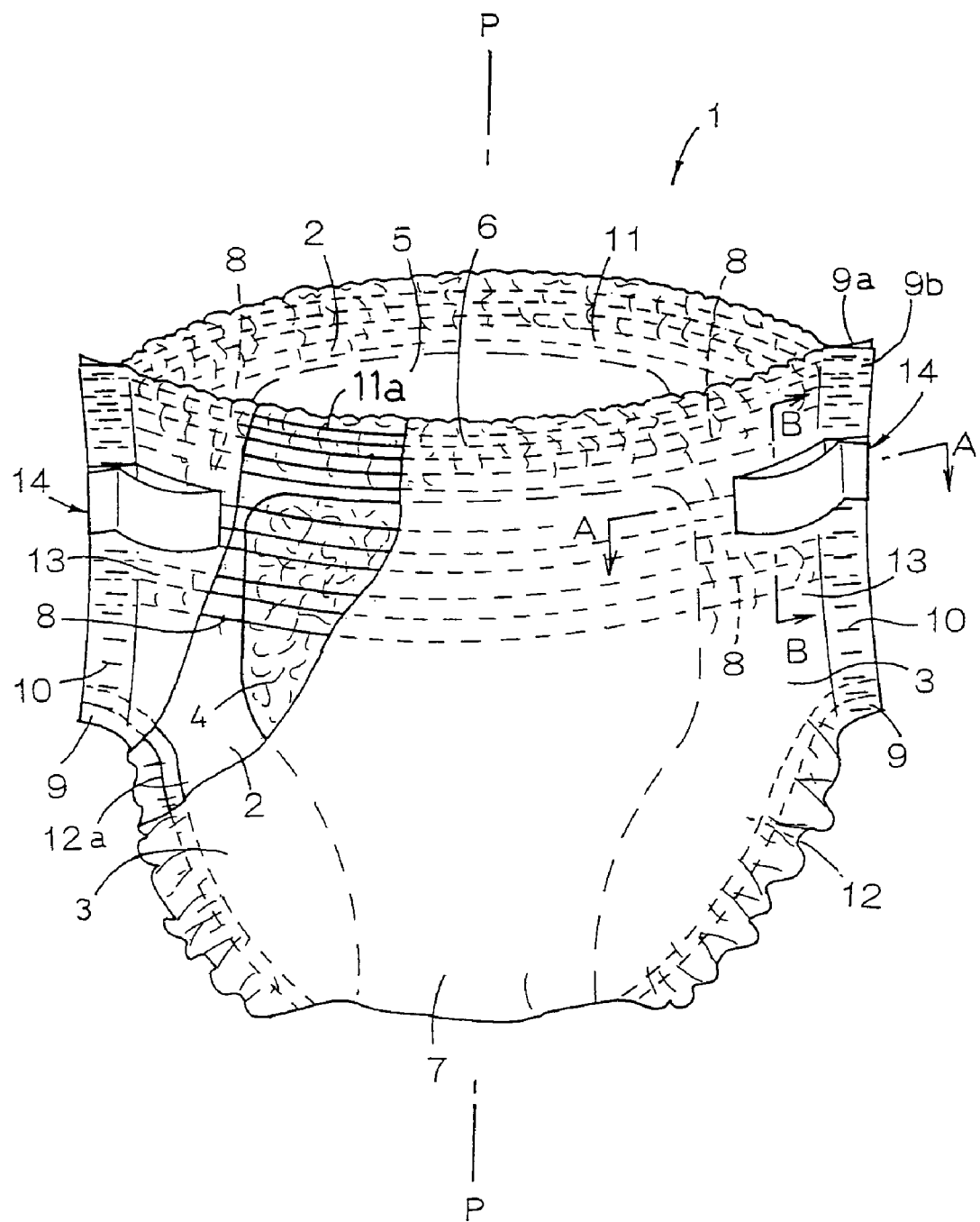
FIG. 1 is a partially cutaway perspective view showing a diaper according to the invention.

A pull-on disposable diaper 1 shown in FIG. 1 in a partially cutaway perspective view comprises a liquid-pervious inner sheet 2 made of nonwoven fabric of thermoplastic synthetic fiber, a liquid-impervious outer sheet 3 made of thermoplastic synthetic resin film and a liquid-absorbent core 4 interposed between these inner and outer sheets 2, 3. The diaper 1 has a waist covering region consisting of a front waist region 5 a rear waist region 6 and a crotch covering region corresponding to a crotch region 7 lying between these waist regions 5, 6. Portions of the inner and outer sheets 2, 3 extending outwardly beyond a peripheral edge of the liquid-absorbent core 4 are joined to each other by means of a hot melt adhesive (not shown). The front and rear waist regions 5, 6 have transversely opposite lateral marginal zones 9a, 9a; 9b, 9b overlaid and joined together by means of sealing lines 10 arranged intermittently along the lateral marginal zones 9a, 9a; 9b, 9b in a vertical direction so that a waist-hole 11 and a pair of leg-holes 12 may be formed. Along peripheral edge zones of the respective holes 11, 12, a plurality of waist-surrounding elastic members 11a and a plurality of leg-surrounding elastic members 12a are interposed between the inner and outer sheets 2, 3 and secured in a stretched state to at least one of these sheets 2, 3 and, therefore, the peripheral edge zones of the respective holes 11, 12 are elastically stretchable and contractible. In the front and rear waist regions 5, 6, a plurality of auxiliary elastic members 8 are provided below the respective waist-surrounding elastic members 11a. In a transversely middle zone of the diaper 1, the elastic elements constituting the respective auxiliary elastic members 8 are interposed between the outer sheet 3 and the core 4 and, in the vicinity of the respective lateral marginal zones 9a, 9a; 9b, 9b, these auxiliary elastic members are interposed between the inner and outer sheets 2, 3 in a stretched state in a waist-circumferential direction. The respective auxiliary elastic members 8 have end zones secured to at least one of the inner and outer sheets 2, 3 at the lateral marginal zones 9a, 9a; 9b, 9b. Portions of the respective auxiliary elastic members 8 lying between the lateral marginal zones 9a and the side edges of the core 4 as well as portions of the respective auxiliary elastic members 8 lying between the lateral marginal zones 9b and the side edges of the core 4 are intermittently joined to at least one of the inner and outer sheets 2, 3. In the diaper 1 formed in this manner, contraction of the respective elastic members causes the respective peripheral edge zones of the waist- and leg-holes 11, 12 as well as the zones defined between the lateral marginal zones 9a and the side edges of the core 4 and the zones defined between the lateral marginal zones 9b and the side edges of the core 4 in the front and rear waist regions 5, 6 to be formed with fine gathers repeating a dent and a bulge one after another in a waist-circumferential direction and a leg-circumferential direction. In the vicinity of the lateral marginal zones 9b, the rear waist region 6 of the diaper 1 is provided on its outer surface with a pair of adhesive tape tabs 14 used to retain the diaper in a rolled up or a folded state.

Figure 2:
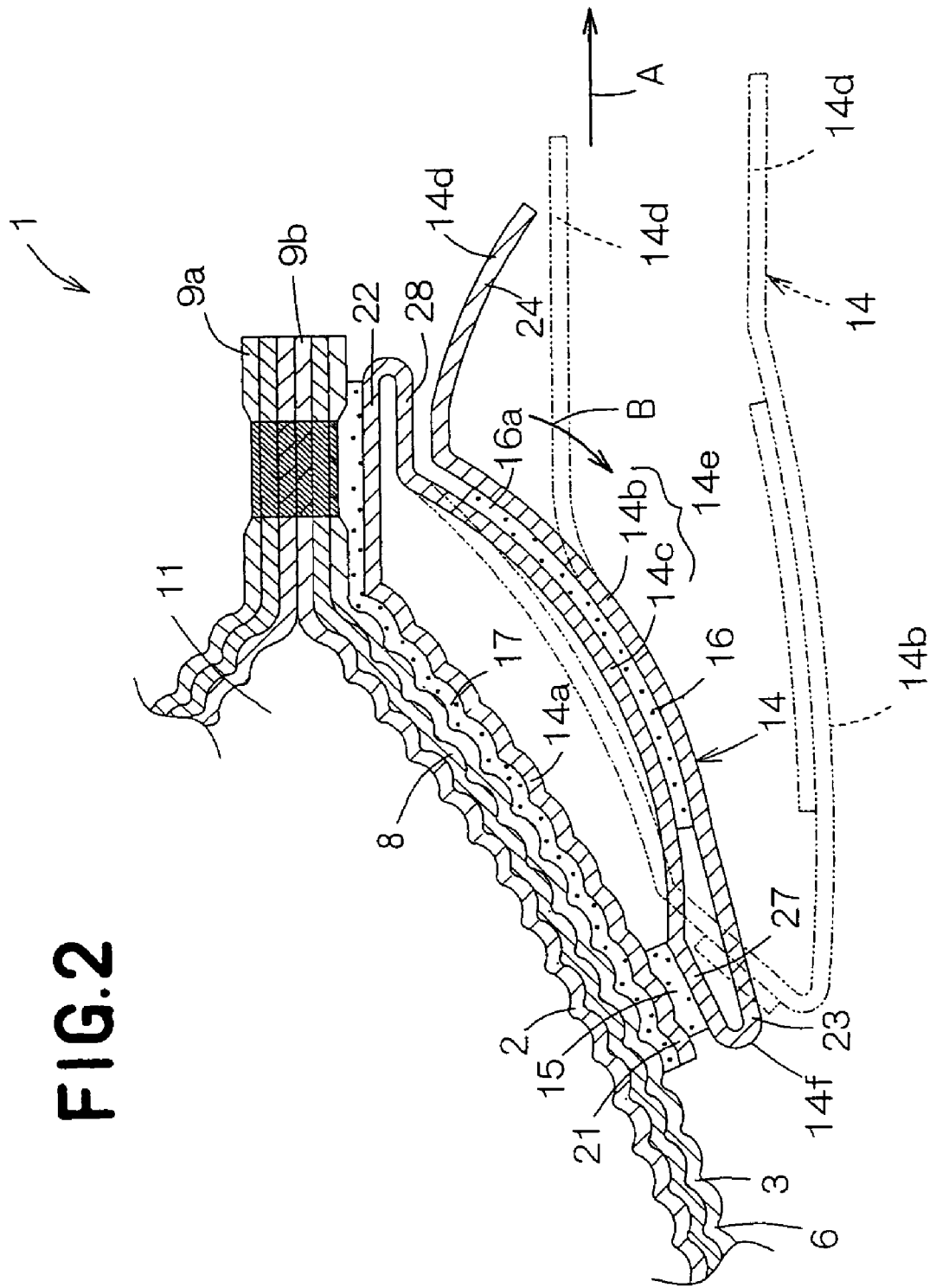
FIG. 2 is a sectional view taken along a line A-A in FIG. 1.
Figure 3:
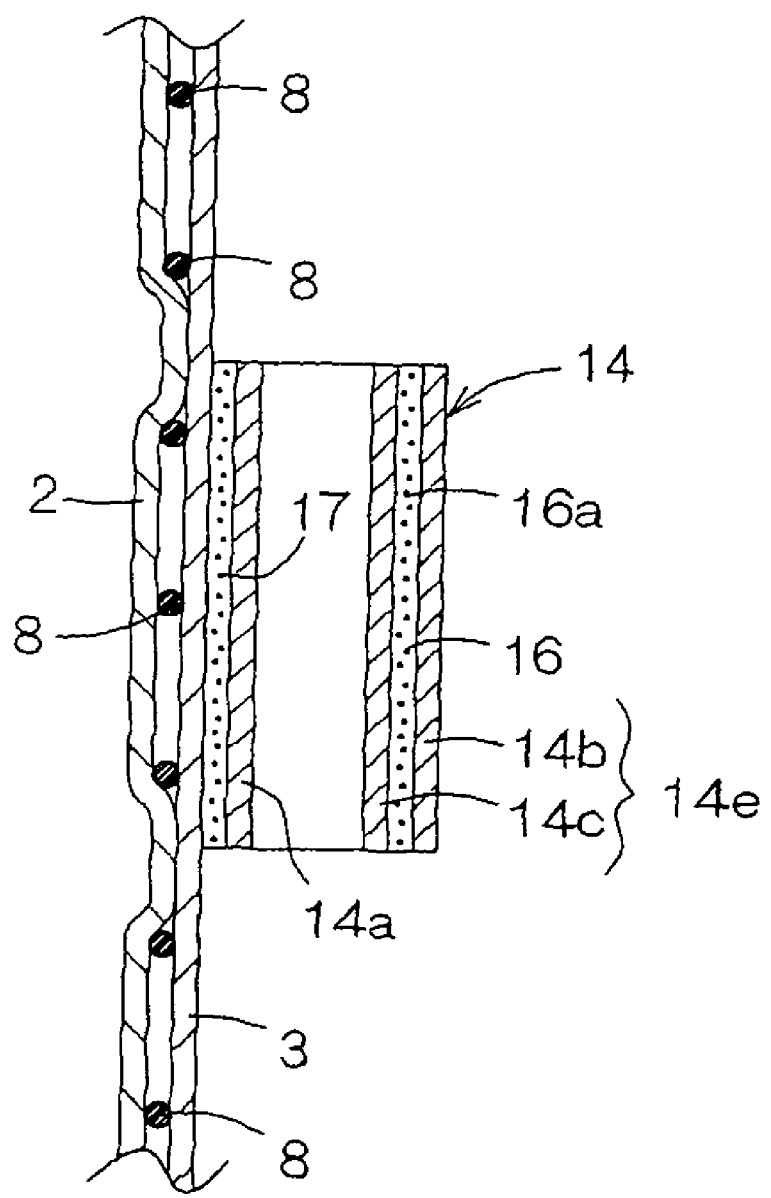
FIG. 3 is a sectional view taken along a line B-B in FIG. 1.

FIG. 2 is a sectional view taken along a line A-A in FIG. 1 and FIG. 3 is a sectional view taken along a line B-B in FIG. 1. Each of the adhesive tape tabs 14 is folded in a Z-shape or a reversed Z-shape as viewed in the waist-circumferential direction. FIG. 2 shows the adhesive tape tab 14 folded in a Z-shaped. This adhesive tape tab 14 may be pulled with a finger grip held rightward as viewed in FIG. 2, i.e., outwardly of the lateral marginal zone 9b in a direction indicated by an arrow A to unfold the adhesive tape tab 14 in its longitudinal direction.

Referring to FIG. 2, the adhesive tape tab 14 comprises a fixed tape section 14a permanently attached to the outer sheet 3 and a movable tape section 14e placed upon the fixed tape section 14a from outside of the diaper 1 and adapted to be substantially deformable for actual use of the diaper 1. The surface of the fixed tape section 14a opposed to the outer sheet 3 defining the outer surface of the diaper 1 is secured to this outer sheet 3 over a substantially entire area of this surface. The fixed tape section 14a has an inner end portion 21 placed aside toward a center line P-P (See FIG. 1) bisecting a width of the diaper 1 and an outer end portion 22 opposite to the inner end portion 21 and placed aside toward the lateral marginal zone 9b, i.e. an opposite end portion of the inner end portion 21. The movable tape section 14e has a distal end portion 24 including a finger grip zone 14d and a proximal end portion 28 being contiguous to the outer end portion 22 of the fixed tape section 14a. The movable tape section 14e comprises a first movable tape subsection 14b and a second movable subsection 14c which are contiguous to each other via a fold 14f and placed upon each other. The first movable tape subsection 14b has a distal end portion 24 and an inner end portion 23 placed aside toward the center line P-P. The second movable tape subsection 14c has an inner end portion 27 being contiguous to the inner end portion 23 of the first movable tape subsection 14b via the fold 14f and a proximal end portion 28 being contiguous to the outer end portion 22 of the fixed tape section 14a. The first movable tape subsection 14b is releasably attached to the second movable tape subsection 14c over an adhesive zone 16a formed by first self-adhesive 16 applied on a zone of the first movable tape subsection 14b opposed to the second movable subsection 14c and being short of the finger grip zone 14d. The second movable tape subsection 14c is, in turn, releasably attached to a zone of the fixed tape section 14a lying aside toward its inner end portion 21 by means of second self-adhesive 15 applied on the inner end portion 27 of the second movable tape subsection 14c opposed to the fixed tape section 14a.

The adhesive tape tab 14 assembled in the manner as has been described above is attached to the outer sheet 3 as the diaper 1 is stretched in a transverse direction so that none of gathers may be left in the regions of the diaper 1 defined between the lateral marginal zones 9a, 9b and the side edges of the core 4. Thereafter, upon contraction of the auxiliary elastic members 8, the inner and outer sheets 2, 3 are formed with fine gathers repeating a dent and bulge one after another in the waist-circumferential direction and thereby these sheets 2, 3 and the fixed tape section 14a also contract in the waist-circumferential direction. The second movable tape subsection 14c opposed to such fixed tape section 14a has its inner end portion 27 releasably attached to the zone of the fixed tape section 14a lying aside toward its inner end portion 21 by means of a second self-adhesive 15 and its proximal end portion 28 contiguous to the outer end portion 22 of the fixed tape section 14a. In a zone defined between the inner end portion 27 and the proximal end portion 28, however, the second movable tape subsection 14c is let free from the fixed tape section 14a (See FIG. 3). With such unique arrangement, the second movable tape subsection 14c also is deformed in its zone defined between the inner end portion 27 and the proximal end portion 28 to curve in the waist-circumferential direction and thereby to bulge in the direction spaced apart outwardly from the front waist region 5, when the inner and outer sheets, 2, 3 and the fixed tape section 14a contract. The first movable tape subsection 14b releasably attached to the second movable tape subsection 14c is also deformed to curve in the same manner as the second movable tape subsection 14c.

In such a state, the second movable tape subsection 14c is curved to bulge in the vicinity of the proximal end portion 28 to which the adhesive zone 16a of the first movable tape subsection 14b is releasably attached. From this state, the finger grip zone 14d of the first movable tape subsection 14b may be pulled in the direction indicated by the arrow A in FIG. 2, in other words, outwardly of the associated lateral marginal zone 9b to peel off the adhesive zone 16a short of the finger grip zone 14d of the first movable tape subsection 14b from the second movable tape subsection 14c in a direction indicated by an arrow B until the first movable tape subsection 14b as shown in FIG. 2 by imaginary lines. The finger grip zone 14d may be further pulled in the direction indicated by the arrow A to peel off the inner end portion 27 of the second movable tape subsection 14c from the fixed tape section 14a and thereby the adhesive tape tab 14 is linearly unfolded outwardly of the associated lateral marginal zone 9b and the first and second movable tape subsections 14b and 14c are released. For the adhesive tape tab of such arrangement, it is unnecessary to reverse a course of the finger grip zone once and then to peel off the tape sections placed upon each other by means of a self-adhesive as the well-known diaper. Obviously, it is possible for this adhesive tape tab 14 also to reverse the finger grip zone 14d once and then to peel off the first movable tape subsection 14b from the second movable tape subsection 14c. Furthermore, it may sometimes occur in the adhesive tape tab 14 that the second movable tape subsection 14c is peeled off from the fixed tape section 14a and thereafter the first movable tape subsection 14b is peeled off from the second movable tape subsection 14c. An effect of the present invention can be found also in such manner of peeling off. The first and second movable tape subsections 14b and 14c have their inner surfaces which are opposed to the outer sheet 3 when the adhesive tape tab 14 is pulled in the direction indicated by the arrow A. It is to be noted that FIG. 2 depicts an example of a state of the adhesive tape tab 14 when the finger grip zone 14d is pulled in the direction indicated by the arrow A by a short distance. In the case of the diaper 1 in a packed condition the first and second movable tape subsections 14b and 14c may be forced to be in contact with the fixed tape section 14a.

Figure 4:
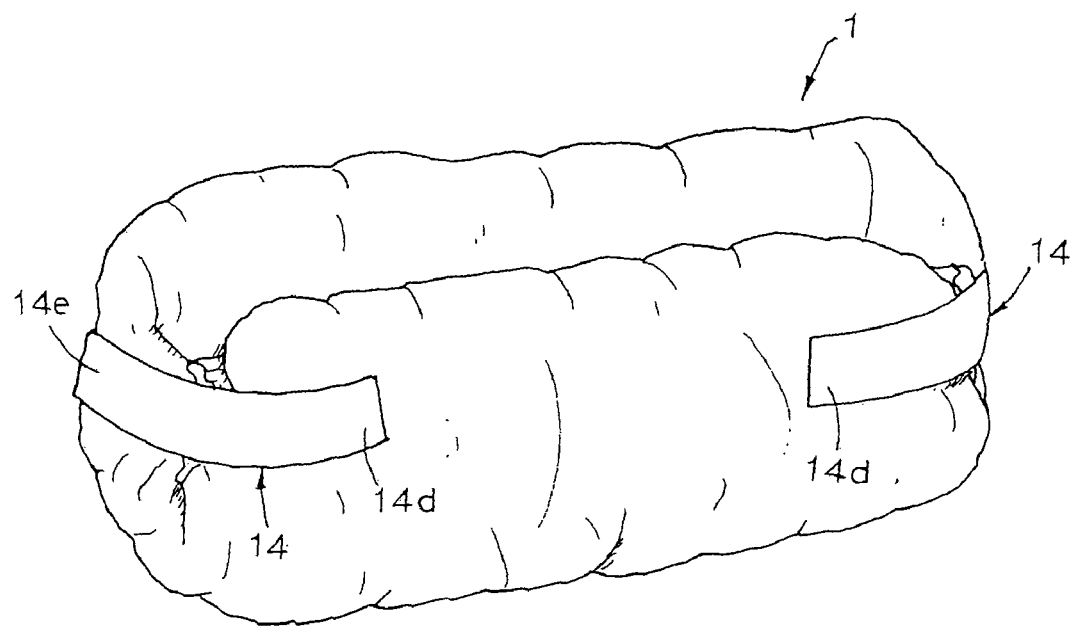
FIG. 4 is a perspective view showing the diaper rolled up for disposal.

FIG. 4 is a perspective view showing the diaper 1 rolled up for disposal. The used diaper 1 can be retained in a rolled up state by fixing the adhesive tape tab 14 unfolded as indicated by the imaginary lines in FIG. 2 to appropriate regions of the diaper 1 utilizing a first self-adhesive 16 applied on the adhesive tape tab 14 as an attaching means. It should be noted that the adhesive tape tab 14 can be used not only to retain the used diaper 1 in a rolled up state but also to take up the slack in the diaper 1 put on the wearer's body in the waist-circumferential direction by appropriately pulling the adhesive tape tab 14 in the waist-circumferential direction.

According the present invention, in the adhesive tape tab 14 the first adhesive 16 coated on the inside surface of the first movable tape subsection 14b can be replaced with such an attaching means as a hook member of a mechanical fastener comprising a set of a hook member and a loop member which are releasably engageable to each other. The hook member is permanently attached to the inside surface of the first movable tape subsection 14b. Of the movable tape section 14e at least the second tape subsection 14c is prepared with a nonwoven fabric or any other material which works as a loop member so as to engage releasably with the hook member on the first movable tape subsection 14b. The outer sheet 3 may be prepared with a nonwoven fabric or a composite sheet of an inside plastic film and an outside nonwoven fabric. The diaper 1 having such a nonwoven fabric can be rolled up into such a state as depicted by FIG. 4, since the hook member can be applied to any part of the outer sheet 3 for engagement therewith.

Figure 5:
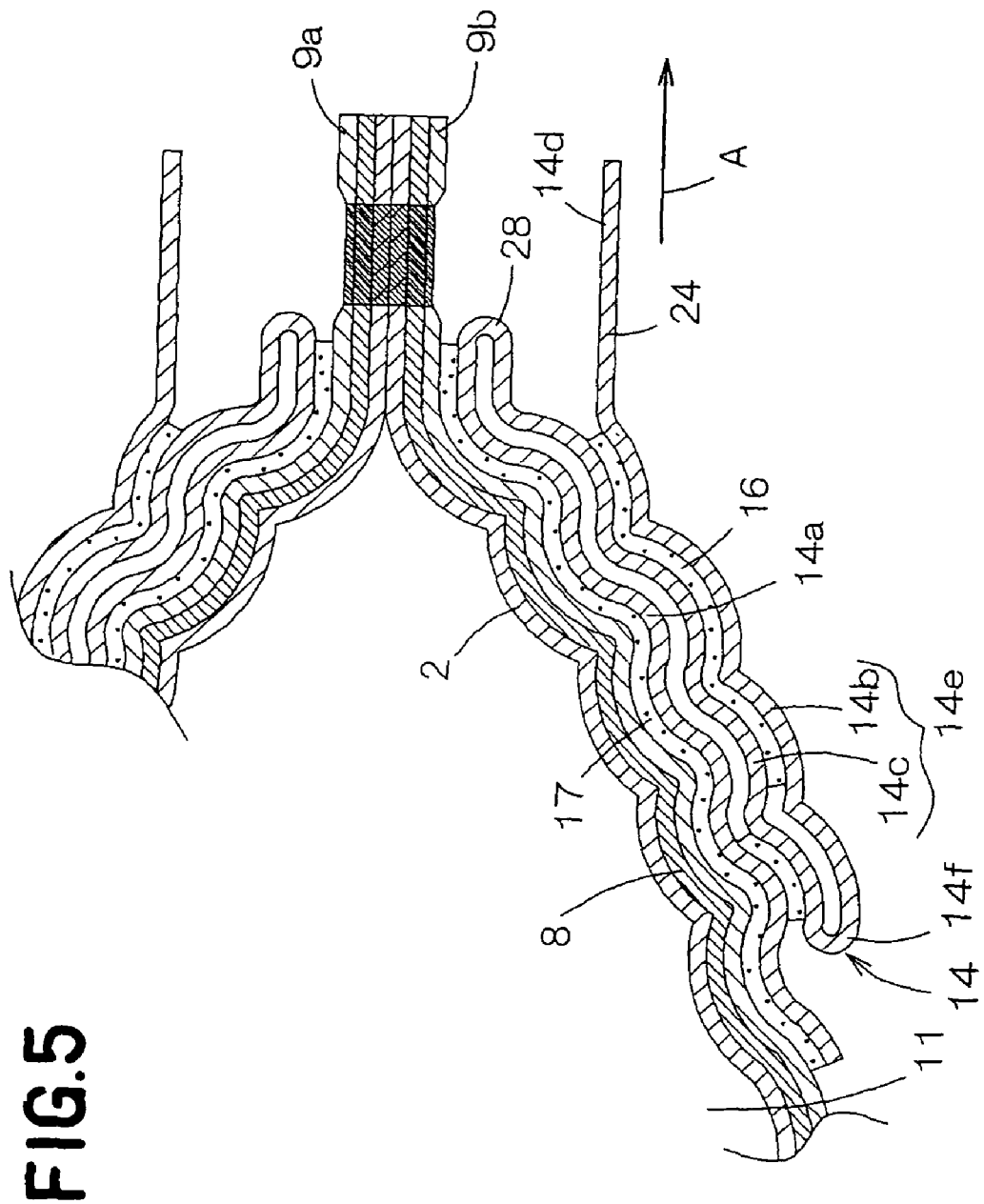
FIG. 5 is a view similar to FIG. 2, showing another embodiment of the invention.

FIG. 5 is a view similar to FIG. 2, showing another embodiment of the invention. In the case of the adhesive tape tab 14 according to this embodiment, the fixed tape section 14a as well as the first and second movable tape subsections 14b, 14c are respectively formed with gathers. In this adhesive tape tab 14 also, the second movable tape subsection 14c curves in the vicinity of the adhesive zone 16a on the tape tab 14 so as to bulge in the direction spaced apart outwardly from the front waist region 5. As a result, the adhesive tape tab 14 may be merely pulled in the direction of the arrow A to be linearly unfolded.

Figure 6:
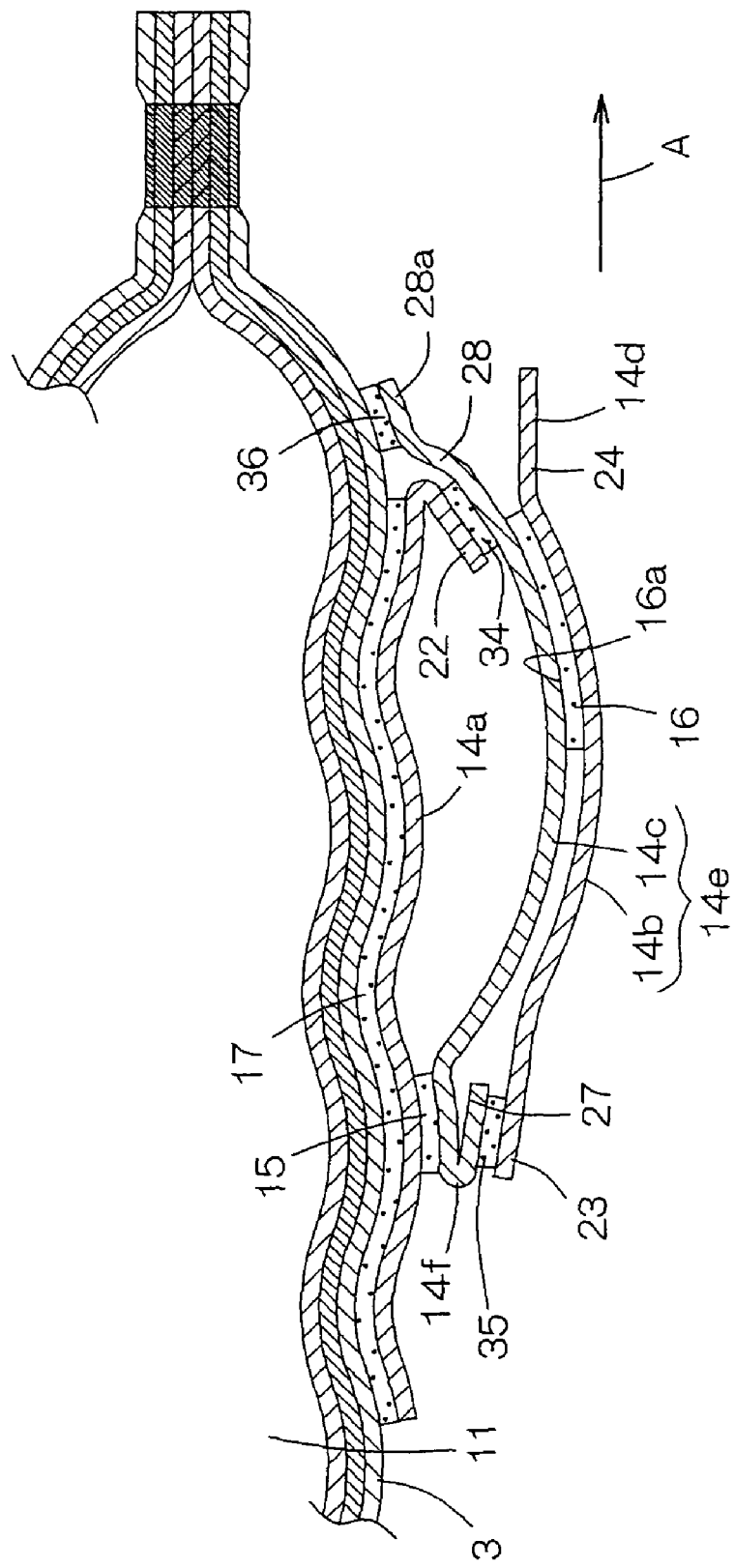
FIG. 6 is a view similar to FIG. 2, showing still another embodiment of the invention.

FIG. 6 also is a view similar to FIG. 2, showing still another embodiment of the invention. The adhesive tape tab 14 according to this embodiment comprises the fixed tape section 14a, the first movable tape subsection 14b and the second movable tape subsection 14c respectively made of separate tabs of plastic film. The outer end portion 22 of the fixed tape section 14a is folded back and secured to the proximal end portion 28 of the second movable tape subsection 14c by means of a fourth adhesive 34. The inner end portion 27 of the second movable tape subsection 14c is folded back along the fold 14f and secured to the first movable tape subsection 14b by means of a fifth adhesive 35. The proximal end portion 28 of the second movable tape subsection 14c has its extremity 28a extending beyond the fixed tape section 14a in the waist-circumferential direction and secured to the outer sheet 3 by means of a sixth adhesive 36. In the case of this adhesive tape tab 14 also, the fixed tape section 14a contracts with formation of the gathers while the second movable tape subsection 14c is curved to bulge outwardly, so the finger grip zone 14d of the first movable tape subsection 14b may be merely pulled in the direction of the arrow A to linearly unfold the adhesive tape tab 14.

According to the present invention, the adhesive tape tab 14 may be formed using a stock material such as a plastic film, a nonwoven fabric, a woven fabric or a laminated sheet consisting of at least two of a plastic film, a nonwoven fabric and a woven fabric. Preferably, the fixed tape section 14a is made of inelastic tape material such as a polyethylene, a polypropylene or a polyester. It is possible to form the movable tape section 14e using an elastic tape material such as a urethane instead of using an inelastic tape material. The fixed tape section 14a and the movable tape section 14e may be formed either by folding a single continuous tape tab or by connecting a plurality of separate tape tabs to one another. These tape tabs preferably have a thickness in the order of 10 to 100µ, respectively. In the embodiment illustrated, contraction of the auxiliary elastic member 8 reduces the dimension of the fixed tape section 14a in the waist region in which the fixed tape section 14a is attached to the diaper 1, it is possible to replace the auxiliary elastic member 8 by the inner and outer sheets 2, 3 which are elastically stretchable in the waist-circumferential direction. In this case, the adhesive tape tab 14 should be attached to the outer sheet 3 which is being stretched together with the inner sheet 2. A position at which each of the adhesive tape tabs 14 is attached to the outer sheet 3 is not limited to the position as shown in Figs. but may be appropriately selected in the waist-circumferential direction. The adhesive zone defined by first self-adhesive 16 applied on the first movable tape subsection 14b of the adhesive tape tab 14 may occupy an extremely restricted area extending short of the finger grip zone 14d. Such arrangement is advantageous in that the adhesive tape tab 14 can be easily unfolded, a quantity of self-adhesive 16 used can be minimized and the adhesive tape tab 14 unfolded in this manner can be quickly anchored on the desired spot of the diaper 1. It is also possible to attach the adhesive tape tab 14 to the outer sheet 3 so as to be placed upon the auxiliary elastic member 8 and thereby to make the curve of the adhesive tape tab 14 more remarkable.

FIG. 7 also is a view similar to FIG. 2, showing further another embodiment of the invention. The adhesive tape tab 14 according to this embodiment also comprises the fixed tape section 14a and the movable tape section 14e. The fixed tape section 14a has its inner end portion 21 folded toward its outer end portion 22. The movable tape section 14e extends in the waist-circumferential direction without being folded. The proximal end portion 28 of the movable tape section 14e is secured to the inner end portion 21 of the fixed tape section 14a by means of a seventh adhesive 47, on one hand, and secured, in its region extending aside from the inner end portion 21 of the fixed tape section 14a toward the center line P-P (See FIG. 1), to the outer sheet 3 by means of a eighth self-adhesive 48, on the other hand. The distal end portion 24 of the movable tape section 14e having the inelastic finger grip zone 14d and the adhesive zone 16a defined by the first self-adhesive 16 applied thereon short of the finger grip zone 14d is releasably attached to the fixed tape section 14a by means of the first self-adhesive 16. The fixed tape section 14a and the movable tape section 14e extend substantially in a same length. If the fixed tape section 14a has a stiffness higher than those of the inner and outer sheets 2, 3, the fixed tape section 14a is not contracted so much as these sheets 2, 3. Consequently, the fixed tape section 14a is deformed to curve in the waist-circumferential direction and thereby to bulge in the direction spaced apart outwardly from the front waist region 5. Particularly when the fixed tape section 14a is secured to the outer sheet 3 by means of an adhesive 17 applied on the fixed tape section 14a intermittently in the waist-circumferential direction as in this embodiment, the fixed tape section 14a tends to bulge between each pair of the spots of the adhesive 17, 17 adjacent to each other. The movable tape section 14e has its adhesive zone 16a formed short of the finger grip zone 14d and releasably attached to the fixed tape section 14a. The adhesive tape tab 14 of such arrangement may be merely pulled with the finger grip zone 14d held by fingers in the direction of the arrow A substantially in a straight line to peel off the movable tape section 14e from the fixed tape section 14a. The adhesive tape tab 14 having been unfolded in this manner can be used not only to retain the used diaper 1 in a rolled up state but also to take up the slack of the diaper 1 put on the wearer's body in the waist-circumferential direction.

FIG. 8 also is a view similar to FIG. 7, showing further another embodiment of the invention. According to this embodiment of the diaper 1, the fixed tape section 14a of the adhesive tape tab 14 is secured to the outer sheet 3 by means of the adhesive 17 applied on the fixed tape section 14a not intermittently but continuously.

In the adhesive tape tabs 14 depicted by FIGS. 5 to 8 the first adhesive 16 coated on the first movable tape subsection 14b may be replaced with a hook member in the same manner as in the adhesive tape tab 14 depicted by FIGS. 1 to 4. If the movable tape tab or the fixed tape tab to be opposed to the hook member of the first movable tape subsection 14b has a nonwoven fabric or other materials which work as a loop member, the first movable tape subsection 14b may releasably engage with the movable tape tab or the fixed tape tab.

FIG. 9 is also a view similar to FIG. 8, showing further another embodiment of the invention. In the diaper 1 of FIG. 9 the adhesive tape tab 14 is replaced with a tape tab 114 which has a movable tape subsection 114e only. The movable tape subsection 114e has an end portion 128 which is permanently attached to the outer sheet 3 by the eighth adhesive 48. A leading end portion 124 of the movable tape subsection 114e has an finger grip zone 114d and a hook member to be used as the attaching means, which is releasably engaged with a part of the outer sheet 3 in FIG. 9. In the neighborhood of the part, the outer sheet 3 bulges outwardly of the diaper 1. The outer sheet 3 is prepared with a nonwoven fabric which is releasably engageable with the hook member 116.

In the pull-on diaper according to the present invention, a tape tab having an attaching means and extending in the waist-circumferential direction comprises a fixed tape section secured to the outer surface of the diaper and the movable tape section being contiguous to the one end portion of the fixed tape section. The movable tape section is formed on its distal end portion with the a grip zone and the attaching means short of the finger grip zone. The attaching means of the movable tape section is releasably attached to a part of the diaper curved to bulge in the direction spaced apart outwardly from the outer surface of the diaper. This unique arrangement ensures that the movable tape section can be released merely by pulling the finger grip zone in the longitudinal direction of the tape tab.

What is claimed is:

1. A pull-on disposable diaper having a waist covering region, a crotch covering region, a waist-hole and a pair of leg-holes and being provided on an outer surface of said waist covering region with a tape tab extending in a waist-circumferential direction of said waist covering region and having an attaching means to be applicable to one of said waist covering region and said crotch covering region, said disposable diaper further comprising:

said waist covering region having a part stretchable and contractible in an elastic manner in said waist-circumferential direction and provided with gathers brought by contraction of an elastic member included in said waist covering region and repeating a dent and a bulge one after another in said waist-circumferential direction;

said tape tab comprising a fixed tape section permanently attached to said outer surface and a movable tape section contiguous to said fixed tape section, said movable tape section having a proximal end portion and a distal end portion, said proximal end portion being contiguous to one end of said fixed tape section in said waist-circumferential direction, said distal end portion having a finger grip zone and lying aside to another end portion opposed to said one end portion of said fixed tape section or lying aside to said one end portion in consequence of folding back of said movable tape section in a vicinity of another end portion;

said attaching means being formed on an inside surface opposed to said outer surface of said waist covering region and located short of said finger grip zone of said movable tape section;

at least a part of said fixed tape section and said movable tape section being curved so as to bulge in a direction spaced apart outwardly from said outer surface of said waist covering region as said waist covering region elastically contracts in said waist-circumferential direction; and said attaching means being releasably attached to said part of one of said fixed tape section and said movable tape section.

2. The pull-on disposable diaper according to claim 1, wherein said one end portion of said fixed tape section is an inner end portion of said tape tab lying aside toward a center line bisecting the width of said diaper, and said end portion opposite to said one end portion is an outer end portion of said tape tab, said movable tape section is folded in two along a fold formed between said distal end portion and said proximal end portion, said movable tape section comprises a first movable tape subsection having said finger grip zone and said attaching means and a second movable tape subsection including said proximal end portion and interposed between said first movable tape subsection and said fixed tape section, said attaching means of said first movable tape subsection is releasably attached to a zone of said second movable tape subsection lying aside to said proximal end portion, and said second movable tape subsection is releasably attached, in a vicinity of said fold, to a zone of said fixed tape section lying aside to said inner end portion and curves so as to bulge in said direction spaced apart outwardly from said outer surface of said waist covering region in a zone to which said attaching means of said first movable tape subsection is releasably attached.

3. The pull-on disposable diaper according to claim 2, wherein said tape tab comprising said first movable tape subsection, said second movable tape subsection and said fixed tape section is folded in a Z-shape or a reversed Z-shape as viewed in said waist-circumferential direction.

4. The pull-on disposable diaper according to claim 2, wherein said second movable tape subsection curves so as to bulge in said direction spaced apart outwardly from said outer surface of said waist covering region in a zone between said inner and outer end portions of said fixed tape section in said waist-circumferential direction.

5. The pull-on disposable diaper according to claim 1, wherein said one end portion of said fixed tape section is an inner end portion of said tape tab lying aside toward a center line bisecting a width of said diaper, and said end portion opposed to said one end portion is an outer end portion of said tape tab, said proximal end portion of said movable tape section lies aside toward said center line and is contiguous to said inner end portion of said fixed tape section, said distal end portion of said movable tape section extends from said inner end portion toward said outer end portion of said fixed tape section and is releasably attached to a zone lying in a vicinity of said outer end portion of said fixed tape section, and said fixed tape section curves in said waist-circumferential direction so that at least said zone of said fixed tape section to which said distal end portion of said fixed tape section is releasably attached bulges in said direction spaced apart outwardly from said outer surface of said waist covering region.

6. The pull-on disposable diaper according to claim 1, wherein said attaching means is an adhesive.

7. The pull-on disposable diaper according to claim 1, wherein said attaching means is a hook member of a mechanical fastener comprising hook and loop members.

8. A pull-on disposable diaper, comprising
first and second waist covering regions,
a crotch covering region extending in a longitudinal direction of said diaper between said first and second waist covering regions,
transversely opposite side edges of said first and second waist covering regions being bonded together at a plurality of bonding sites to define a waist-hole and a pair of leg-holes,
at least a tape tab on an outer surface of said first waist covering region, said tape tab having an attaching element attachable to one of said second waist covering region and said crotch covering region,
an elastic member which is attached to a part of said first waist covering region, renders said part of the first waist covering region elastically stretchable and contractible in said waist-circumferential direction, and forms gathers in said elastically stretchable and contractible part of said first waist covering region as a result of contraction of the elastic member,
said tape tab comprising a fixed tape section which is directly permanently attached to said outer surface of the first waist covering region, and a movable tape section which is not directly permanently attached to said outer surface of the first waist covering region,
said movable tape section having a proximal end portion and a distal end portion,
said proximal end portion being connected to said fixed tape section,
said distal end portion having said attaching element on an inner surface thereof,
the inner surface of said distal end portion facing said outer surface of said first waist covering region,
said attaching element being directly releasably attached to one of (i) the fixed tape section,
(ii) a portion of the moveable tape section, and (iii) the gathers,
said movable tape section defining a curve that bulges away from said outer surface of said first waist covering region, thereby facilitating release of said attaching element from said one of (i) the fixed tape section, (ii) a portion of the moveable tape section, and (iii) the gathers when said movable tape section is pulled.

9. The pull-on disposable diaper according to claim 8, wherein the attaching element is directly releasably attached to the proximal end portion of the moveable tape section, and said proximal end portion defines said curve.

10. The pull-on disposable diaper according to claim 9, wherein the proximal end portion having opposite inner and outer ends,
the outer end of the proximal end portion being connected to the fixed tape section;
the inner end of the proximal end portion being connected to the distal end portion and releasably attached to the fixed tape section.

11. The pull-on disposable diaper according to claim 10, wherein the proximal end portion further comprises a middle section between the inner and outer ends;
said middle section being free of direct attachment to the fixed tape section; and
said middle section including opposite inner and outer surfaces, the inner surface facing the fixed tape section and the outer surface being directly releasably attached to said attaching element.

12. The pull-on disposable diaper according to claim 11, wherein said middle section defines only one said curve.

13. The pull-on disposable diaper according to claim 11, wherein said middle section defines a plurality of said curves which, in turn, define a wavy shape of both said middle section and the attaching element directly releasably attached to said curves.

14. The pull-on disposable diaper according to claim 11, wherein at least one of (a) the fixed tape section and the outer end of the proximal end portion, (b) the inner end of the proximal end portion and the distal end portion, are non-contiguous one to another.

15. The pull-on disposable diaper according to claim 8, wherein the attaching element is directly releasably attached to the fixed tape section, and a segment of the movable tape section between said attaching element and said proximal end portion defines said curve.

16. The pull-on disposable diaper according to claim 15, wherein said fixed tape section is permanently directly attached to the outer surface of the first waist covering region at a plurality of intermittently arranged locations between which said fixed tape section is not directly attached to the outer surface of the first waist covering region.

17. The pull-on disposable diaper according to claim 8, wherein the attaching element is directly releasably attached to the gathers, and a segment of the movable tape section between said attaching element and said fixed tape section defines said curve.

* * * * *